(12) United States Patent
Wijay et al.

(10) Patent No.: US 8,211,004 B1
(45) Date of Patent: Jul. 3, 2012

(54) ADJUSTABLE DEVICE FOR THE TREATMENT OF FEMALE URINARY INCONTINENCE

(76) Inventors: Bandula Wijay, Friendswood, TX (US); Ayaz Mahmud Durrani, Sugar Land, TX (US); Nandhika Wijay, Friendswood, TX (US); Omar Hayat Durrani, Houston, TX (US)

( * ) Notice: Subject to any disclaimer, the term of this patent is extended or adjusted under 35 U.S.C. 154(b) by 310 days.

(21) Appl. No.: 12/157,596

(22) Filed: Jun. 11, 2008

(51) Int. Cl.
*A61F 2/02* (2006.01)
(52) U.S. Cl. ......................................................... 600/30
(58) Field of Classification Search .................... 600/29, 600/30, 37; 128/885; 606/151
See application file for complete search history.

(56) References Cited

U.S. PATENT DOCUMENTS

| | | | |
|---|---|---|---|
| 5,836,314 A | 11/1998 | Benderev et al. | 128/898 |
| 6,786,861 B1 | 9/2004 | Pretorius et al. | 600/31 |
| 6,929,663 B2 * | 8/2005 | Rioux et al. | 623/23.64 |
| 7,083,568 B2 | 8/2006 | Neisz et al. | 600/30 |
| 7,229,404 B2 | 6/2007 | Bouffier | 600/30 |
| 7,261,723 B2 | 8/2007 | Smith et al. | 606/139 |
| 7,862,502 B2 * | 1/2011 | Pool et al. | 600/37 |

* cited by examiner

*Primary Examiner* — Christine Hopkins
(74) *Attorney, Agent, or Firm* — Kajane McManus (57) ABSTRACT

A support device suitable for urethral support is adjustable for length post operatively. An elongated body has at least one bellows and a line going through a passage in the elongated body. The elongated body is supported in the patient and the line is adjustable by balloon inflation or rotation of a drum. The amount of support can be changed postoperatively using an instrument inserted through the skin with a local anesthetic or even from outside the skin with no surgical intervention. The bellows changes length when adjustments are made.

7 Claims, 6 Drawing Sheets

ADJUSTABLE DEVICE FOR THE TREATMENT OF FEMALE URINARY INCONTINENCE

FIELD OF THE INVENTION

This disclosure is for a novel device to suspend the female urethra thereby supporting the urethra for the treatment of female stress incontinence. The device comprises a sling that is suspended from the pubic bone and contains an inflatable balloon that on inflation or deflation and/or a ratchet mechanism that tensions a pull string which regulates the degree to which the urethra is compressed.

BACKGROUND OF THE INVENTION

Stress urinary incontinence is an involuntary loss of urine on a sudden rise in the abdominal pressure as in coughing, sneezing or lifting weight. This happens when the urethra closes incompletely due to intrinsic deficiency of the muscles of urethra or hyper mobility of the urethra. Normal urethral muscle function and the normal anatomical contour of the urethra are altered due to over stretching of pelvic organs during vaginal deliveries. Obesity also brings about similar changes in the urethra. Diabetes causes deterioration of nerves and muscles of urethra. Chronic cough due to smoking or other lung conditions is also a risk factor in causing stress incontinence of urine. Stress urinary incontinence varies in the degree of loss of control. It may consist of occasional leakage of a few drops of urine or it may amount to severe loss of urine needing several diapers a day. Most of the time, it interferes in the normal social life of the persons. In severe cases it becomes a big expense for diapers.

Stress urinary incontinence is rare in men. Most commonly it is due to injury to the muscles and the nerves of urethra that may occur in radical prostatectomy for the cancer of the prostate.

The treatment of stress urinary incontinence can be tried with non-surgical methods. This consists of developing strength in the muscles of urethral sphincter by Kegel exercises. Dr. Arnold Kegel, a gynecologist, has popularized exercises that he designed to strengthen the pelvic floor muscles that work on the urethra. These exercises could be helpful in early cases or could strengthen the muscles before the symptoms develop. A vaginal pessary, which consists of a stiff ring, can be placed in the vagina to press against the urethra to prevent leakage until the bladder contracts to expel the urine. A pessary is often not easy for the patient to insert or remove. As a result, a physician usually inserts the pessary into the patient. In Addition, a pessary can induce vaginal infection.

Surgical treatment is the mainstay in stress incontinence of urine. In some cases walls of the urethra can be approximated by injecting contigen via a cystoscope. Contigen is like a thick gel and it is made from bovine tissue. It acts like a bulking agent to approximate the walls of the urethra. However, because it is a foreign material, patient has to undergo allergy test for it. After it is injected, contigen has the tendency to gradually leak out and the injection has to be repeated. Besides contigen, some other bulking materials are also available. However, these bulking agents are successful in very few cases.

The main aim in all surgical procedures for stress urinary incontinence is to give support under the urethra against which the urethra is compressed when abdominal pressure suddenly rises as in coughing, sneezing or lifting heavy objects. Several operations have been in vogue over the time. In Marshall Marchetti Krantz urethropexy and in Birch urethropexy, the procedures are carried out through an abdominal approach. These procedures are more invasive and have longer recovery time. Laparoscopic approach through the abdomen has also decreased in popularity.

The most commonly performed procedures for stress urinary incontinence are the sling procedures. These procedures have some variations, but all are comparatively minimally invasive surgeries. They all are based on using a sling under the urethra to compress it so that leakage of the urine is prevented during a sudden rise in the abdominal, and consequently the bladder, pressure during coughing, sneezing or lifting heavy objects. While this condition is not fatal, the inconvenience and the lack of freedom for women to control the urge to urinate affect a woman's lifestyle. There are variations in the sling material such as autologous rectus fascia, porcine skin, homologous fascia, and synthetic sling. There are some variations in the approaches to sling placement. The sling can be placed through supra-pubic approach, vaginal approach, or an obturator approach. As discussed earlier, the most common method for the treatment of female urinary incontinence is to suspend the urethra using an implantable sling. In the past, slings have been supported in different ways in the abdominal region. Most common of these methods is to support the urethra include suspending form the pubic bone.

Benderer et. al in U.S. Pat. No. 5,836,314 discloses a procedure for treating female stress incontinence. In his method, Benderer suggests the use of suspension sutures to sling the urethra and one or more bone anchors in the pubic bone to suspend the sutures.

Most of the traditional surgical methods for implantable and non-implantable devices are very complicated and cumbersome to use. Any surgical intervention, especially in the pelvic region, is very complicated, requiring long recovery and ambulation.

Bouttier in U.S. Pat. No. 7,229,404 B2 describes a device for suspending the urethra using a sling and anchors.

Smith et. al. in U.S. Pat. No. 7,261,723 B1 describes a device sling apparatus that is delivered using a needle handle from below the urethra. The device is also suspended from above to provide the compression on the bladder neck.

Johan et. al in U.S. Pat. No. 7,083,568 describes a sling wherein the sling apparatus can be permanently changed during and or after implantation.

Pretorius et. al. in U.S. Pat. No. 6,786,861 B1 describes a method by which a distensible member is inserted dorsally between the urethra and the pubic bone. By inflating the distensible member via a valve, the distensible member constricts the urethra.

In almost all cases, slings made from a biocompatible material, such as polypropylene, have been used to suspend the bladder neck. Various means to suspend the sling have also been disclosed by many inventors.

Invariably, the sling is hung from either the abdominal wall or from the pelvic bone. Various attachment methods also have been disclosed. In spite of the many inventions, and the devices that materialized subsequently, female stress incontinence is still essentially unresolved, proving that a simple solution to this annoying problem is still needed. In light of the fact that the physiology of the ailment changes post operatively, it is essential that one would consider a device that can adjust the degree to which the urethra is pinched post operatively, and after few weeks or months.

The present invention discloses such methods wherein the device can be adjusted either by a ratcheting mechanism or by inflating balloon that in turn tugs on the sling, compressing or decompressing the bladder neck and/or a combination of the ratchet mechanism and balloon inflation. It is preferred to use a non-distensible balloon for this purpose rather than distensible balloon, as distensible balloons will have a tendency to push the inflating mediums due to the elastomeric forces associated with them.

The major problem with all the previous sling procedures is that there is no control on the amount of tension they place on the urethra. The surgeon only guesses the amount of tension he should leave in the sling. During surgery, the patient is usually under general anesthesia. The body is completely relaxed. Therefore, during the operation, the tension on the sling is different than when the patient is no longer under anesthesia. Also, during surgery, the patient is lying down, and the position of the bladder and the urethra is different to when the patient is standing up and in walking state. In the first few days after surgery, there is some edema and swelling due to the surgical trauma. The tension of the sling is comparatively higher during this period, and the sling may get too loose after the swelling subsides. Once the sling is placed and the surgery is completed, there is no way to alter the tension on the sling. Because of these reasons, there is a considerable failure rate in these types of surgeries. As one would expect, there are some cases where the sling is too loose and the surgery has not succeeded in alleviating the urinary stress incontinence. In other cases, the sling is too tight and the patient cannot urinate. The patient would need catheterization to empty the bladder until another surgery is performed to loosen the sling.

The amount of the pressure exerted by the sling on the urethra can be a significant issue. If the degree of pressure is low, the incontinence is not cured. On the other hand, if the pressure is high, the urethra would not allow urine pass on active voluntary contraction of the bladder. This delicate balance in the degree of compression needed to achieve normal urination cannot be achieved through guessing or trial and error. Presently, none of the procedures for the treatment of stress urinary incontinence have any control on the degree of compression placed on the urethra. The novel device presented here is the only device where the compression placed on the urethra is adjustable.

In addition, clinical evidence has shown that the current procedure to cause complications of infection resulting in osteitis. The suspension of the sling on the pubic bone with metallic or non-metallic screws, and similar fasteners, has resulted in other complications, as the screws are not very stable, and can even detach from the bone. As such, one aspect of the present invention recommends that the sling be hung and supported in the periostium of the pubic bone ramus.

SUMMARY OF THE INVENTION

A device supports the bladder neck and urethra and is minimally invasive to implant. It comprises:
1. A sling to support the urethra;
2. An anchor consisting an inflatable balloon from which the sling is suspended; and
3. An implanted fluid reservoir through which the fluid can be transferred into the balloon on the anchor.

The proposed sling; unlike slings that have been disclosed in the past (which are mainly polypropylene mesh devices that are often distensible) is preferably a flexible and non-distensible thin-walled tube. The tube preferably has a 3-4 mm. diameter. As the tube is thin-walled, when used as a sling, it will take the shape of a flat belt. The sling tube is typically made from nylon, polyester, irradiated polyethylene, or polypropylene. The tube is made from a bi-axially oriented polymer such that the tube is preferably neither able to expand in diameter or length when a circumferential or lengthwise force is applied. The sling can be silicone coated to minimize tissue adhesion.

The non-distensible character of the sling prevents, or minimizes, stretch and yield with time due to the abdominal pressure or urge pressure by the patient. Therefore, the sling will not appreciably relax with time, reducing its ability to compress the urethra.

The sling has a neck region at both ends containing an accordion type feature allowing the sling to lengthen or shorten just like an accordion would lengthen or shorten when pulled or pushed. This feature allows the surgeon to adjust the sling length during the procedure.

The sling also has a non-stretchable ribbon having strings attached to it at both ends, preferably made from woven polyester, nylon, or silk, and is best when made to a flat ribbon. The ribbon is placed inside the sling tube. Pulling on the ribbon causes the sling to shorten and thereby compressing the urethra. Similarly, releasing the ribbon will allow the sling to lengthen due to the accordion feature, enabling the urethra to decompress.

Thus, the sling is able to provide compression on the urethra by applying tension on the ribbon, which is inside the sling tube. The tension in the ribbon provides the means to adjust the degree to which the sling compresses the urethra.

The sling components are preferably non stretchable and non distensible to prevent creep and yield after the implantation of the sling.

The anchor is also an implantable component, which is placed above or near the pubic bone. Unlike in previous inventions, the anchor of the present invention is not attached to the pubic bone by means of screws or fasteners. Instead, the anchor is provided with at least one tag, (preferably two) with suture holes in it. The anchor is attached to the pubic ramus, and the anchor can be placed in front of, above, or behind the pubic bone.

The anchor contains two receptacles for the attachment of the sling. These receptacles have such geometric character that the "barbs" on the sling snap securely when inserted. The anchor may be made from any biomaterial with sufficient strength to hold the sling without significant flexing or yielding.

The string of the sling passes over the anchor and is knotted after the surgeon determines the degree to which the sling should be tensioned, which depends on the actual anatomy of the patient.

The anatomy of different patients is different, requiring slings of different lengths, and this is resolved during surgery by the surgeon selecting the sling of the correct length and accordion.

The anchor also contains the inflatable body, which on inflation tugs on the ribbon, which in turn compresses the urethra.

The inflation chamber can be constructed from any biocompatible plastic such as nylon polyester, polypropylene, or silicone. It is preferred that the inflation chamber is made from a material that is not elastomeric, such as silicone rubber, but made from a non distensible balloon, such that there will be no elastomeric forces that could squeeze fluid out of the inflation chamber after implantation.

The anchor should be sufficiently stiff to provide adequate support in order to support the sling. Additionally, a stiffener may be placed within the anchor to provide adequate support in order to hang the sling, which may be made from stainless steel, titanium, or stiff plastic.

The implanted reservoir holds the fluid that is used to inflate the balloon on the anchor. This fluid reservoir can be a separate component, or it may be designed as part of the anchor system. In any case, the purpose of this reservoir is to allow the surgeon to inflate or deflate the balloon with fluid, from outside, after device has been implanted and after the surgically induced swelling has subsided.

The fluid reservoir is implanted just under the skin. When additional tug on the sling is required, fluid can be injected into the reservoir using a needle through the skin accessing the reservoir chamber.

The reservoir chamber, typically about 5 mm in diameter and 2 cm long, can be approached through the skin whenever the surgeon locates the port side with his fingers. The chamber in turn contains two sub-chambers. A mechanical valve made from suitable rubber is provided to separate the fluid chamber from the first chamber to prevent contact of the fluid chamber with the body tissue. The valve prevents leakage of fluid out of the chamber. As such, the first chamber separates the actual fluid chamber from the tissue and prevents tissue growing into the valve and causing valve malfunction.

Alternatively, the fluid chamber can be activated by a piston mechanism whereby the piston is advanced and retracted by turning a screw. This is accomplished by inserting a tiny screw drive through the skin after infiltration of local anesthetic like lidocaine.

The anchor may also be designed such that turning the screw will tug on the ribbon as an alternative to the fluidic means to tug on the ribbon.

In summary, the present invention comprises a urethral sling for the treatment of female stress incontinence having a preferably non-distensible sling, which can accordion in order to compress the urethra. This functionality is accomplished by tugging on a ribbon, which is located within the sling sheath. The ribbon is secured to an anchor, which is sutured to the pubic ramus bone. The anchor consists of either an inflatable, non-distensible balloon, or a mechanism, to tug on and adjust the tension on the ribbon by either fluidically inflating the balloon or by mechanically winding the thread ends of the ribbon on a spool using mechanical means.

Therefore, this invention allows the surgeon to adjust the degree to which the sling compresses the urethra during and immediately after the surgical implantation of the urethra sling, or after some weeks or months post surgery.

DETAILED DESCRIPTION OF THE PREFERRED EMBODIMENT

Figure 1:
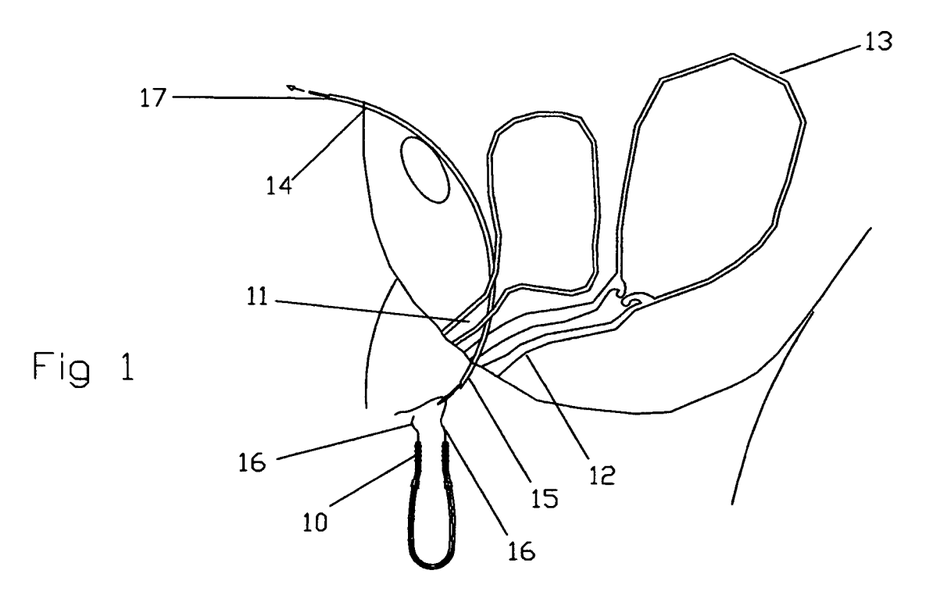
FIG. 1 shows a diagrammatic anatomic view of the pelvic region of the human female human and the general method of the introduction of a needle to pull a urethral sling.

FIG. 1 is an anatomic description of the pelvic region of the human female. The proposed urethral sling 10 is introduced just below the urethra 11 in the space between the urethra 11 and the vagina 12 bilaterally using a curved needle 14 introduced anteriorly and behind the pubic bone on either side of the urethra. Typically the surgeon creates a pocket between the urethra 11 and vagina 12 where the sling 10 will be placed. The needle 14 can be made blunt or sharp. If it is made sharp, the physician must wear a thimble on his finger to receive the needle when it is pushed from above. When the needle 14 is made hollow, it enables the operator to thread a loop guide wire 15 to facilitate threading of the pull thread 16 through the needle. The thread 16 is pulled through the needle 14 along with the sling 10 until one end of the sling 10 exits the skin at the location 17 where the needle 14 was introduced. The same process is repeated so that the other end of the sling 10 is pulled on the opposite side of the urethra 11 the same manner until the sling 10 and the pull thread 16 exits the skin at which place the needle 14 entered.

Figure 2:
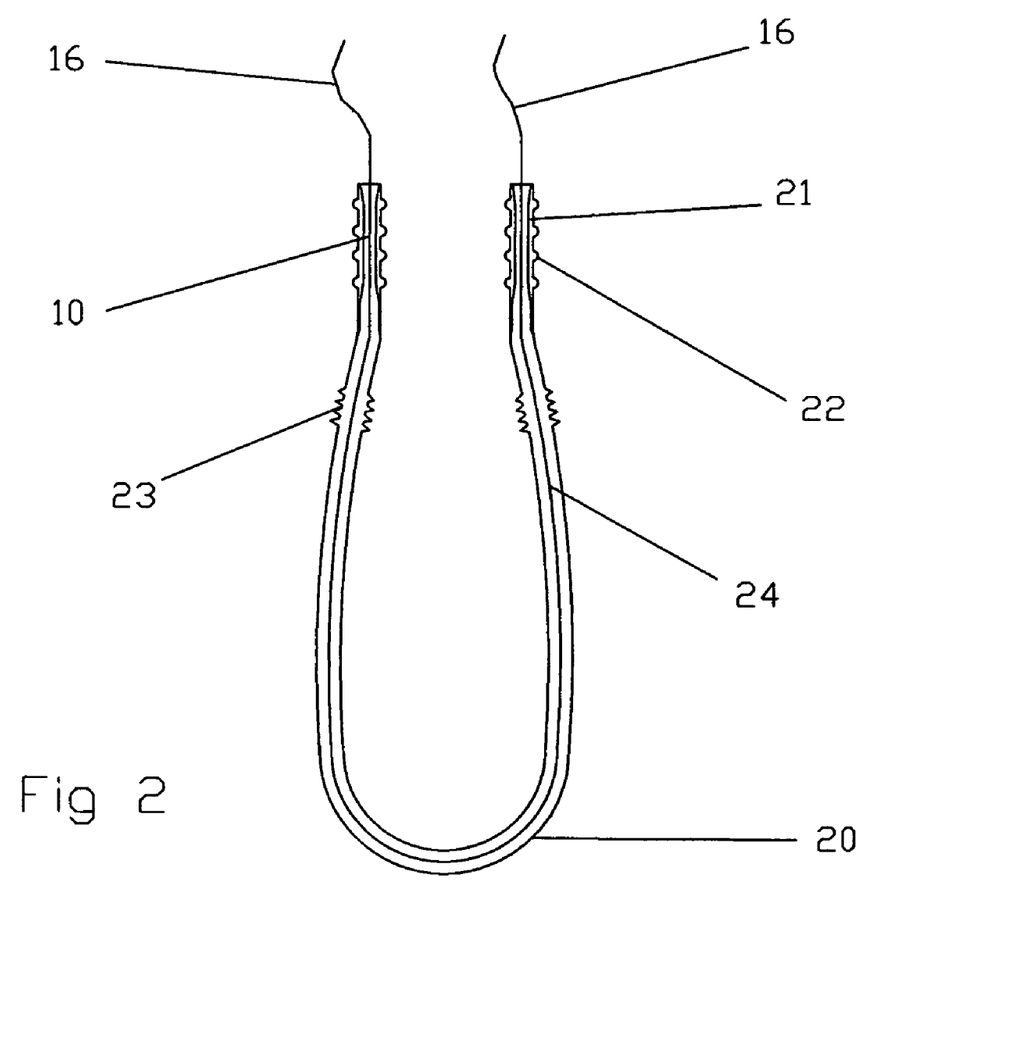
FIG. 2 shows a diagrammatic view of the proposed sling.

FIG. 2 is a diagrammatic representation of the sling. The sling 10 consists of a tubular portion 20 that is made from a thin wall plastic material such as Nylon, Polyester (PET), Polyester (PBT), Polyethylene, Polypropylene, and other suitable material. The sling 10 is a long elongated tube that is bi-axially or uni-axially oriented in order to impart strength. The sling 10 can also be made from Silicone rubber. The sling 10 has a neck region 21 which is an elongated tube structure containing "barbs" 22. The barbs 22 are circular in nature, or they can also simply be simply protrusions that are segments of a circular ring. The barbs 22 can be rounded or teeth like. The sling 10 also contains an area that has an accordion or bellows feature 23 such that the sling 10 can expand and contract by stretching or relaxing the accordion portion 23 of the sling 10. The pull member 24 has the preferred shape of a ribbon and is placed within the sling 10. This is typically a ribbon in shape and is made from a strong material such as molecular oriented material such as Nylon, Polyester, or multithreaded silk, or suture materials such as catgut. The pull member 24 is used to pull or relax on the sling 10 to constrict or relax the urethra 11.

Figure 3:
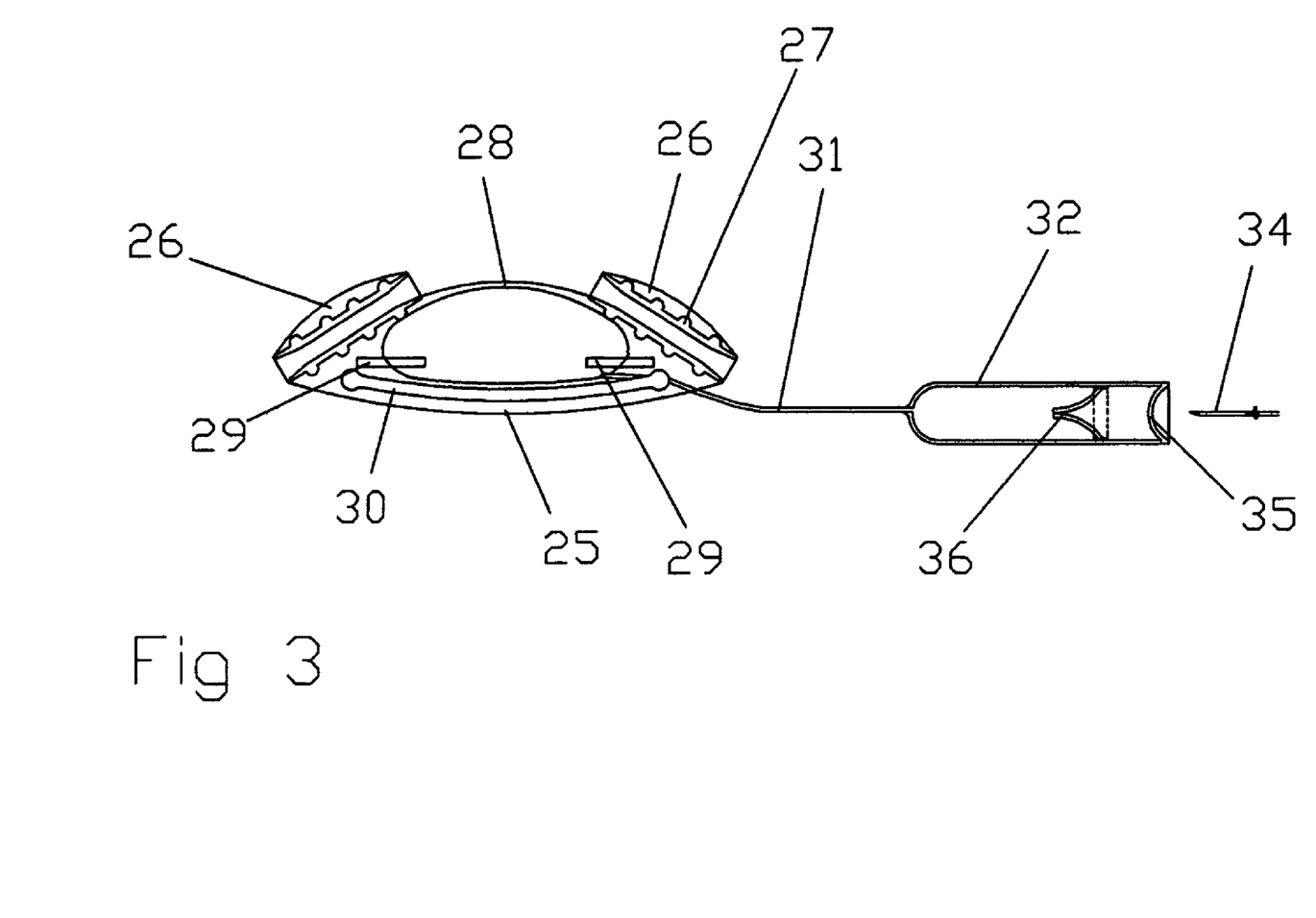
FIG. 3 shows a diagrammatic view of the suspender to which the sling is attached and one alternate method for inflating the balloon that is used to tension the pull threads.
Figure 3A:
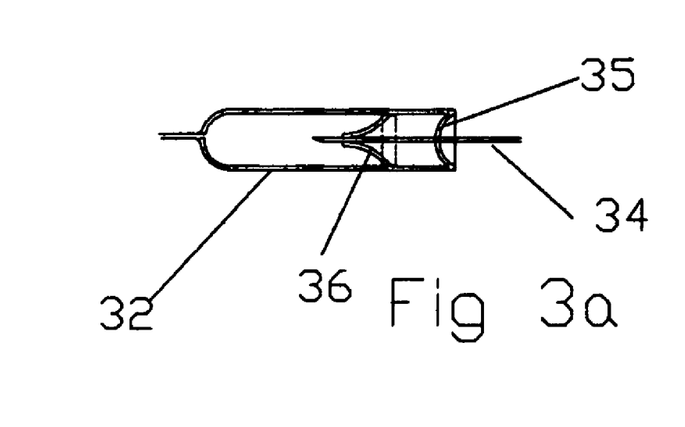
FIGS. 3a and 3b show the means for inflating the balloon using a syringe needle and an alternate syringe to inflate the balloon in the suspender.
Figure 3B:
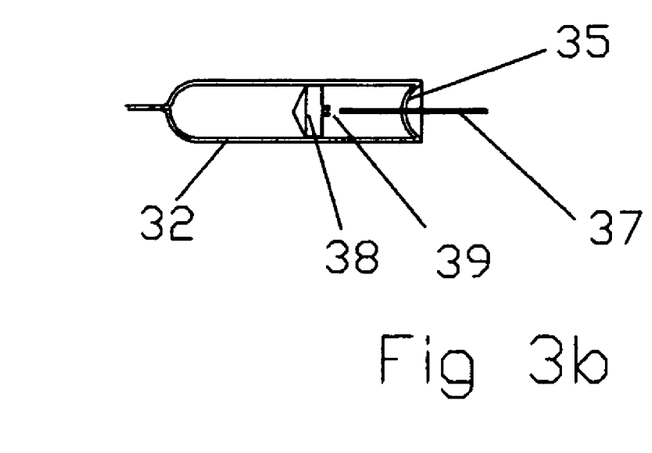

FIG. 3 shows the sling suspender 25. The suspender 25 has two tubes 26 on either side made part of the suspender 25. The suspender 25 is made from a suitable plastic such as Nylon, Polypropylene, and Silicone, etc. The tube members 26 have corrugations 27 in the inner surface to accept the barbs 22 of the sling 10. When the sling neck 21 is pulled through the tube 26 of the suspender 25, the barbs 22 will engage with the corrugations 27 on the tube 26 and the sling neck 21 will lock in place securely. The thread ends 16 are then brought over and tied above the suspender 25. The suspender 25 has an inflatable balloon 28. The balloon 28 can be made as an integral part of the suspender 25 or can be a separate element. The balloon 28 can be made from an elastic or elastomeric material. The suspender 25 contains one or two suture tabs 29 to suture and anchor the suspender 25 to the adjoining tissue. A stiffener member 30 can be an integral part of the suspender 25, either molded into it or subsequently placed in the suspender 25 in channel made available (not shown) in the suspender 25. The balloon 28 is inflated or deflated with a suitable fluid such as saline containing contrast solution for enhanced radio opacity. This is done via the connecting tube 31 from a small implanted syringe 32, shown in FIG. 3A. The syringe 32 is especially designed with two membranes 35 and 36. The first membrane 35 is made typically from an elastomeric rubber and the membrane 36 is made in the form of a dovetail valve that will allow a syringe needle 34 to go through easily without puncturing and when the needle 34 is removed will close and seal fully due to the back pressure created in the balloon compartment. The needle 34, which is introduced through the skin, will puncture through the membrane 35 but will enter the membrane 36 without puncturing that membrane. Fluid is introduced or withdrawn to inflate or deflate the balloon 28. The inflation of the balloon 28 will tension the pull threads 16, thereby pulling on the sling 10 and hence constricting the urethra 11. On the other hand, by deflating the balloon 28 by withdrawing the fluid, the tension on the strings 16 will be reduced, thereby relaxing the pull threads 16 and hence the sling 10 and relaxing the urethra 11. Alternatively, the syringe 32 can be designed with a plunger 38, as shown in FIG. 3B, having a receptacle 39 that can accept a screwdriver 37. By advancing the plunger 38, the balloon 28 can be inflated, or retracting the plunger 38 can deflate the balloon. By doing so, the pull threads 16 and/or the tube members 26 can be tensioned or relaxed, thereby constricting or relaxing the urethra 11.

Figure 4:
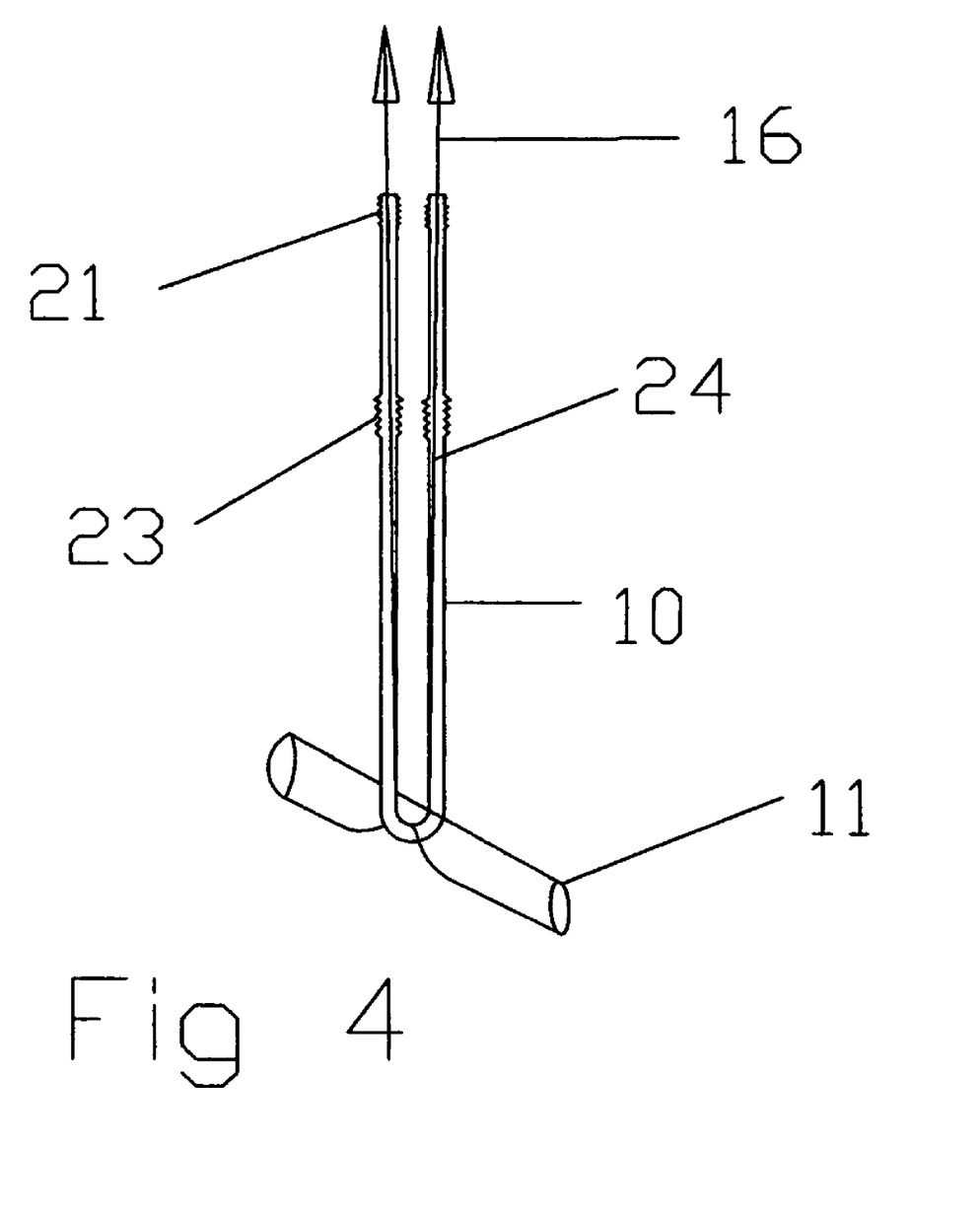
FIG. 4 shows the operating principle of the proposed sling device.

FIG. 4 diagrammatically explains the principal of the proposed sling 10. The sling 10 is made from a material that does not stretch substantially. For this reason bi-axially oriented tube material is ideal for this purpose. Such can be made from Nylon, Polypropylene, polyethylene etc. The accordion 23 enables some degree of adjustability in order to provide the expansion and contraction needed for the fine adjustment. The barbed region 21 can be made long enough that it can be trimmed to suit the patient to be treated. For example, a larger female may require a longer sling length while a more petite female may require a shorter sling length. As such the sling 10 can be trimmed at the barbed portion 21 to make it suitable for the patient undergoing the procedure. As shown in FIG. 4, by tensioning the sling 10, the urethra 11 can be constricted. And if the surgeon has over stressed the urethra 11 during the operation, it can be relaxed by reducing the tension of the pull thread 16. Actually, it is very difficult for the surgeon to estimate the degree to which the sling 10 should be pulled up during surgery as he cannot estimate the inflammation of the tissue post procedure. The proposed device enables the surgeon to go back and adjust the tension and adjust the sling 10 to make it more comfortable for the female to urinate.

Figure 5:
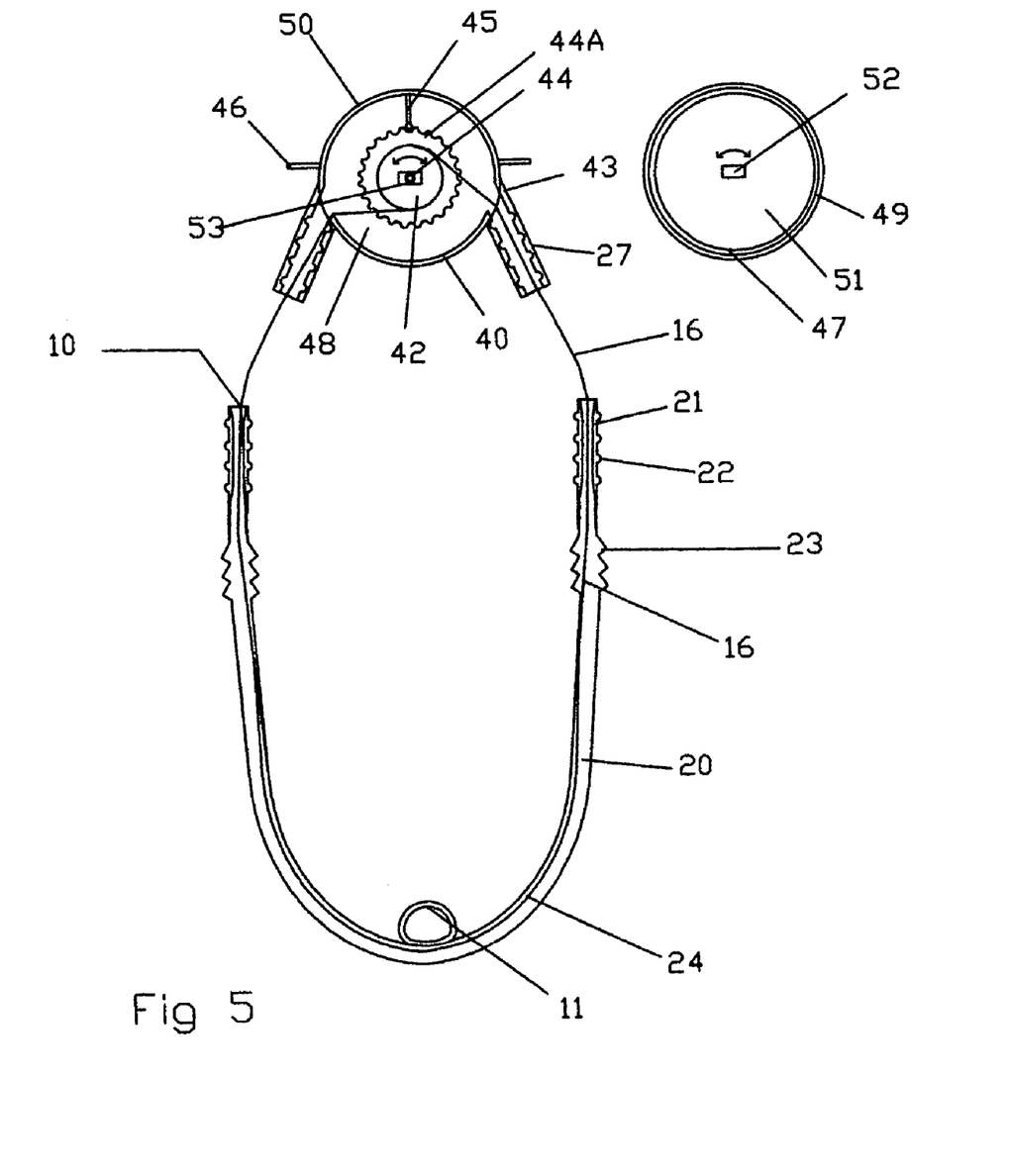
FIG. 5 shows an alternate method of a sling suspender that has a spool and a ratchet mechanism to pull on the pull threads to tension or relax the sling.

FIG. 5 is a diagrammatic representation of the proposed sling 10 with a suspender 40 similar to the one earlier presented 25 in FIG. 3 except that tensioning is done by winding the pull threads 16 on to a spool or drum 42. The sling used in this alternate method is identical to the sling in FIG. 2. The barbs 22 engage to the corrugations 27 of the tube structure 43 to attach the sling to the suspender 40. The spool 42 is located at the center of the suspender housing 40 and rotates over a spindle 44. The ratchet wheel 44A is an integral part of the spool 42. A trip member 45 locks the ratchet wheel 44A. When the ratchet wheel 44A is turned it will ride over the trip member 45 and keeps the ratchet wheel 44A locked into a place set by the operator. The ratchet wheel 44A can be turned either way to tension or relax the pull on a line made from a suitable thread material 16. The trip member 45 can be made as an integral part of the suspender housing 40 or it can a separate component attached by suitable means. The tabs 46 allow the suspender to be sutured to the tissue using normal sutures and help to stabilize the suspender 40. The space 48 is free and can be filled with saline. The cover 47 has a rim 49 that snaps to the rim 50 of the suspender 40. This snap mechanism can be designed using many methods available for a lid so long as such snap connection provides a hermetic seal. The face of the cover 47 is elastomeric and contains a pocket 52 that accepts a screwdriver blade. The pocket 52 engages with the receptacle 53, which is an integral part of the ratchet wheel 42. By turning the pocket 52, one is able to turn the ratchet wheel 44A. Once the pocket 52 is let go, it reverts back to its normal position without turning the ratchet wheel 44A. This is because it is necessary to press on the pocket 52 to engage the receptacle 53. In other words, in order to turn the wheel 44, one must push on the pocket 52 so as to engage the receptacle 53.

The entire assembly, the sling and the suspender 40 is hermetically sealed. Once the sling is in place as previously described, and the sling neck 21 is pushed into the tubes 27 of the suspender 40, the pull wires 16 are wrapped around the spool 42 such that the turning of the spool 42 winds the pull threads 16. Once the ratchet wheel 44A is turned to reach the right tension of the pull threads 16, the inside space 48 of the suspender 40 is washed and cleaned with saline and filled with saline. The cover plate 47 is then snapped on to the suspender 40 and the suspender 40 is sutured to the adjoining periostium of the pubic bone tissue. The skin incision is closed in the usual manner.

Within a few weeks after the surgery, and after the edema has subsided, the surgeon can, under local anesthesia adjust the tension of the pull threads 16 by turning the ratchet wheel 44A using a screw driver introduced through the skin to turn it either direction to tension or relax the pull thread 16. On the other hand, it is also possible to provide a knob instead of the pocket 52 such that the knob can be turned without having to puncture the skin in order to turn the ratchet wheel 44A as the wheel 44A can be manipulated under skin without having to create an incision.

The above description of the device invented here is an introduction of the concepts. No effort was made to provide any engineering details of construction and is not our intension to provide such details. As such, this prosthesis can be redesigned to appear different and can be made from a variety of bio-compatible materials. The advantage of the device is its ability to adjust the sling tension, by a variety of methods, with the preferred techniques described above, immediately after, or a few days or weeks after the surgery, which is not possible in the various previous inventions and products. The sling in the above invention will not attach to the tissue due to its smooth surface and will enable the surgeon to adjust the tension. In addition, it has the accordion feature that allows adjustment in length during and or after sling implantation. The pull threads are located inside the sling tube and are not in contact with body tissue. As such the pull thread will not form "adhesion" with the body tissue allowing free movement required for adjustment. The suspension component of the sling is placed above the pubic bone and is sutured to the tissue to generally anchor the suspender. The sling portion is attached to the suspender using the barbs and the corrugations, and once attached, will provide a hermetic seal.

The operation uses two curved needles that are introduced through a small incision in the skin just above the pubic bone and exit on either side of the urethra in the space between the urethra and the wall of the vagina. The invention discussed here proposes a hollow needle with a sharp obturator to facilitate the process of pushing the needle, as discussed above. It is important that the physician wear a thimble in his gloved finger to receive the needle.

The device discussed above will enable the female to control the urinating function and will be an excellent solution to the problem of incontinence faced by the millions of patients worldwide.

The above description is illustrative of the preferred embodiment and many modifications may be made by those skilled in the art without departing from the invention whose scope is to be determined from the literal and equivalent scope of the claims below.

We claim:

1. An implantable medical device to provide internal organ support for a patient, comprising:

an elongated body adapted to internally support an internal organ and having thereon a pair of fixation locations to accomplish said support;

a length adjustment feature associated with said body to facilitate post operative length adjustment to optimize the function of the internal organ;

said elongated body is tubular and said adjustment feature comprises a line extending through a passage in said body;

wherein said line is wound or paid out off a drum, and;

wherein said drum is engaged to a ratchet to allow said drum to hold selected clockwise or counterclockwise rotations.

2. The device of claim 1, wherein:

said drum and ratchet are mounted in a sealed housing;

said passage in said body is sealed into said housing; and said passage and said housing contain a fluid.

3. The device of claim 2, wherein:

said housing comprises a rotatable cover and is flexible for selective engagement with said drum.

4. The device of claim 3, wherein:

said cover comprises a receptacle for rotation of said cover with said drum using an insertable instrument.

5. The device of claim 3, wherein:

said cover comprises a knob that may be manipulated without surgical intervention.

6. The device of claim 3, wherein:

movement of said line changes the length of at least one bellows in a wall of said body.

7. An implantable medical device to provide internal organ support for a patient, comprising:

an elongated body adapted to internally support an internal organ and having thereon a pair of fixation locations to accomplish said support;

a length adjustment feature associated with said body to facilitate post operative length adjustment to optimize a function of the internal organ;

said elongated body is tubular and said adjustment feature comprises a line extending through a passage in said body;

said line is wound or paid out off a drum;

wherein movement of said line changes the length of at least one bellows in a wall of said body, said body capable of supporting the urethra, and;

wherein said drum is supported on a structure that engages a wall of said elongated body through engagement of projections and depressions between said structure and the wall of said elongated body.

* * * * *